(12) United States Patent
Hodge (10) Patent No.: US 12,083,019 B2
(45) Date of Patent: Sep. 10, 2024

(54) LATERAL AND MEDIAL PIVOTING KNEE PROSTHESIS

(71) Applicant: William Andrew Hodge, Scottsdale, AZ (US)

(72) Inventor: William Andrew Hodge, Scottsdale, AZ (US)

( * ) Notice: Subject to any disclaimer, the term of this patent is extended or adjusted under 35 U.S.C. 154(b) by 452 days.

(21) Appl. No.: 15/746,200

(22) PCT Filed: Jul. 21, 2016

(86) PCT No.: PCT/US2016/043333
§ 371 (c)(1),
(2) Date: Jan. 19, 2018

(87) PCT Pub. No.: WO2017/015458
PCT Pub. Date: Jan. 26, 2017

(65) Prior Publication Data
US 2020/0085583 A1     Mar. 19, 2020

Related U.S. Application Data

(60) Provisional application No. 62/195,367, filed on Jul. 22, 2015.

(51) Int. Cl.
*A61F 2/38*     (2006.01)
*A61F 2/30*     (2006.01)

(52) U.S. Cl.
CPC .......... *A61F 2/3859* (2013.01); *A61F 2/3868* (2013.01); *A61F 2/3877* (2013.01); *A61F 2/389* (2013.01); *A61F 2002/30237* (2013.01); *A61F 2002/30245* (2013.01); *A61F 2002/30934* (2013.01)

(58) Field of Classification Search
CPC .......... A61F 2/38; A61F 2/3836; A61F 2/384; A61F 2/3845; A61F 2/385; A61F 2/3854; A61F 2/3859; A61F 2/3868; A61F 2/3886; A61F 2/389
See application file for complete search history.

(56) References Cited

U.S. PATENT DOCUMENTS

| | | | |
|---|---|---|---|
| 5,219,362 A | 6/1993 | Tuke | |
| 6,013,103 A | 1/2000 | Kaufman | |
| 2005/0096747 A1 | 5/2005 | Tuttle | |
| 2005/0107886 A1 | 5/2005 | Crabtree | |
| 2009/0265011 A1* | 10/2009 | Mandell | A61F 2/38 623/20.15 |
| 2015/0257889 A1 | 9/2015 | Kang | |

* cited by examiner

*Primary Examiner* — Marcia L Watkins
(74) *Attorney, Agent, or Firm* — McHale & Slavin, P.A.

(57) ABSTRACT

The present invention comprises an implantable knee prosthesis for the arthritic, aging, ligament-deficient knee having a femoral component, a tibial component and patella component forming three interactive knee compartments mainly the lateral, medial, and femoral patellar compartments articulating together with a variable axial pivot type of knee motion. This novel design accomplishes this motion pattern with four femoral component radii coacting with four reciprocal proximal tibial surface recesses. This occurs in a laterally congruent axial pivot fashion during the first half of knee flexion creating efficient external femoral rotation to align the femoral-patellar groove with the patella/quadriceps muscle complex.

18 Claims, 8 Drawing Sheets

LATERAL AND MEDIAL PIVOTING KNEE PROSTHESIS

PRIORITY CLAIM

This application is national stage filing from PCT/US16/43333 filed on Jul. 20, 2016 which claims priority to United States provisional patent application 62/195,367 filed on Jul. 22, 2015, the contents of which are expressly incorporated by reference.

INCORPORATION BY REFERENCE

All references cited herein are expressly incorporated by reference.

BACKGROUND OF THE INVENTION

Disease, age and trauma take their toll on the cartilage of the knee to the point where no cartilage remains and pain is experienced due to bone on bone contact.

Knee prosthesis for replacement of a knee joint damaged due to injury or disease generally includes femoral and tibial components to provide new contact surfaces for the joint. These device try to mimic the motion of a healthy knee and rely on the medial condyle for the primary pivot point.

Koo et al: have shown that the knee moves in a laterally pivoting motion during walking. Koo, Seung bum and Andriacchi, Thomas P., *The knee joint center of rotation is predominantly on the lateral side during normal walking*, Journal of Biomechanics 41 (2008); 1269-1273.

Kozanek et al, teach that knee kinematics is dependent on load and flexion and that motion of the knee cannot be generalized to a single pattern. Koznanek, Michal et al, *Tibiofemoral kinematics and condylar motion during the stance phase of gait*, Journal of Biomechanics, 42, (2009); 1877-1884.

Hoshino and Tashman teach sliding in the medial compartment occurs in some movement and corresponds to a lateral pivot at least during running. Hosino, Yuichi and Tashman, Scott, *Internal tibial rotation during in vivo, dynamic activity induces greater sliding of tibio-femoral joint contact on the medial compartment*, Knee Surg Sports traumatol Arthrosec 20 (2012): 1268-1275.

Banks et al: has shown with Fluoroscopic 3 dimensional imaging, that in the knee with anterior cruciate ligament (ACL) deficiency (99% of total knee replacements are ACL deficient), the motion pivots about the lateral compartment in the first half of the flexion cycle. Also, this motion allows for early engagement of the patella/quadriceps muscle complex providing optimal strength. Banks, Scott A, et al.; Making Sense of Knee Arthroplasty Kinematics: News You Can Use; Journal of Bone & Joint Surgery, Vol. 85A Supplement 4.

Hodge et al. has shown wear patterns in arthritic knees demonstrate a lateral pivoting wear out foot print which has been measured. Similar wear out patterns were seen in traditional total knee arthroplasty ("TKA"). Hodge, W A et al.; Journal of Arthroplasty, Vol 24, Issue 3, pp 448-453 (April 2008).

Tuttle et al., U.S. Pat. No. 7,261,740 teach a medial approach to knee replacement in which the medial condyle slides and pivots during extreme motion.

Kauffman et al, U.S. Pat. No. 6,013,103 teaches a medial approach to knee replacement with a knee prosthesis for replacing at least a portion of a knee joint between the distal end of a femur and the proximal end of a tibia. The knee prosthesis includes a tibial component for mounting to the proximal end of the tibia, this tibial component including a proximal surface having a hemispherical medial compartment and a lateral compartment; and a femoral component for mounting to the distal end of the femur, this femoral component including a hemispherical medial condylar portion for pivotally coacting with the hemispherical medial compartment of the tibial component and including a hemispherical lateral condylar portion for movably coacting with the lateral surface of the tibial component; the hemispherical medial condylar portion being substantially congruent with the hemispherical medial compartment of the tibial component so that substantially complete surface-to-surface contact between the hemispherical medial compartment of the tibial component and the hemispherical medial condylar portion of the femoral component is provided throughout the range of flexion of the knee joint.

The prior art approaches to knee replacement try to mimic the motion of a normal healthy knee. These approaches however, conveniently ignore the fact that as the body ages and ligaments deteriorate, normal healthy motion is no longer possible. The present invention takes into account that the knee being replaced is no longer a normal healthy knee and reengineers the pivot points to accommodate the mechanical realities of an aging body. This means the pivot point in the present invention is artificially moved from the medial condyle to the lateral condyle to accommodate the aging mechanical condition of the knee in walking (weight bearing) activities, but then can switch to activating a different (more medial) rotation during higher flexion activities like kneeling and squatting.

While the literature suggests the need for incorporation of a "stable" (a guided, controlled, contained, predictable, smooth, regular motion which eliminates slipping, irregular, erratic and unpredictable motions), lateral pivot during the initial half of the flexion cycle, no such designs have been forthcoming. More specifically, nothing in the known prior art discloses or suggests a knee prosthesis including a tibial component for mounting to the proximal end of the tibia, the tibial component including a proximal surface having a hemispherical lateral compartment and a medial compartment; and a femoral component for mounting to the distal end of the femur, the femoral component including a hemispherical lateral condylar portion for movably coacting in a pivoting fashion with the hemispherical lateral compartment of the tibial component in the first half of the knee flexion cycle, but also allowing medial pivoting motion during the latter half of the knee flexion cycle; the hemispherical lateral condylar portion being substantially congruent with the hemispherical lateral compartment of the tibial component so that substantially complete surface-to-surface contact between the hemispherical lateral compartment of the tibial component and the hemispherical lateral condylar portion of the femoral component is provided throughout the first half of the flexion cycle of the knee joint. The pivot is lateral during approximately the first 50% of the flexion cycle but shifts more medial during the final 50% of flexion motion when the lateral compartment congruency lessens allowing more translational movement in this compartment causing the pivot point to shift medially.

BRIEF SUMMARY OF THE INVENTION

The present invention allows the arthritic knee to pivot opposite of a normal healthy knee for better efficiency during most weight bearing activities (high load) such as walking and stair climbing.

The present invention provides a knee prosthesis for replacing at least a portion of a knee joint between the distal end of a femur and the proximal end of a tibia which allows for improved movement, stronger function and lower wear.

The knee prosthesis of the present invention includes, in general, a tibial component for mounting to the proximal end of the tibia, the tibial component including a concave proximal surface having a hemispherical lateral compartment and a medial compartment; and a femoral component for mounting to the distal end of the femur, the femoral component including a convex hemispherical lateral condylar portion for coacting in a pivoting fashion with the hemispherical lateral compartment of the tibial component. The convex hemispherical medial femoral condylar portion having substantial translational motion on the concave tibial articular surface by having less congruency in the AP plane while remaining congruent in the coronal plane with the curved half-pipe shaped medial compartment of the tibial component. There still is significant ball & socket type contact in the hemispherical lateral compartment providing the lateral pivot point during the first half of the flexion cycle of the knee It is an object of the invention to improve the range of motion (ROM) by keeping knee contact points posterior in the knee thereby avoiding bone impingement.

It is an object of the invention to improve knee strength by better dynamic alignment and mechanical advantage of the quadriceps mechanism by keeping the femoral condyle facing the patella/quadriceps muscle accomplished by the lateral pivoting motion during early flexion while the lateral femoral condyles is anchored in this posterior socket on the tibial surface thereby creating strong leverage (increase quadriceps moment arm) during walking, stair climbing and sit to stand activities. Later in the flexion cycle, this pivot point shifts medially.

It is an object of the invention to improve durability of the knee by motion of this design with controlling the existing erratic arthritic knee motion through substituting the 'variable pivot' motions which lock the pivoting condyle in place while the opposite condyle glides and thereby lower the articular surface stress which in turn imparts less stresses at the bone-implant interface. This occurs since artificial implant surfaces do not force 'normal' knee motion which had only been enabled in nature by 'normal' ligaments.

It is an object of the invention to improve durability of the knee by providing ample knee contact surfaces with congruent stable motion providing low articular surface stresses compatible with the implant's biomaterials during walking, stair climbing and sit to stand activities.

It is an object of the invention to provide a less invasive surgery than currently required for many existing knee designs since surgeons have the surgical options of leaving the patient's remaining ligaments and bone largely intact.

It an object of the invention to not require the additional surgical step of a lateral release of the patella since the implant dynamically self-aligns the femoral-patella groove with the natural lateralized position of the patella/quadriceps mechanism which inserts into the tibial tubercle.

It is an object of the invention to induce the femur to self-align with the patella/quadriceps muscle by the variable axial pivoting motion occurring pivot during flexion) as the knee flexes thereby permitting the patella to smoothly engage the femoral-patellar groove enhancing stability and strength of the knee.

It is an object of the invention to permit the aging, arthritic knee to move in a laterally pivoting fashion in the first half of flexion cycle, then switch to a medial pivoting motion during later flexion seen with the aging arthritic knee).

It is an object of the invention to reduce the need for separate implant designs to accommodate different existing arthritic conditions regardless of cruciate ligament damage; i.e requiring a posterior stabilized technique with a post and cam a more aggressive surgical technique as well as a different implant concept.

It is an object of the invention to take advantage of the properties of new biomaterials such as ultra-high molecular weight polyethylene (UHMWPE), cross linked polyethylene with vitamin E, metallic materials such as cobalt-chromium or titanium, but may be formed from other materials, such as metals, a ceramic material, a polymer material, a bio-engineered material, carbon fiber, nylon, glass, polyethylene, polyester, polytetrafluoroethylene or the like, in other embodiments. These materials may be used alone or in combination with various metals, ceramics and coatings.

It is an object of the invention to provide a knee implant which can be personalized during implantation to a patient's own anatomy and knee motion.

It is an object of the present invention to provide a knee prosthesis specifically designed to provide substantially complete surface-to-surface contact between the congruent articular implant surfaces of a lateral femoral condyle and its reciprocal proximal surface of a tibia throughout a significant range of weight bearing flexion of the knee joint.

It is an object of the present invention to provide a knee prosthesis specifically designed to induce variable pivoting motions about the longitudinal axes of the femur and tibia as the knee flexes during different activities. This is accomplished during walking, stair climbing and chair rising by restricting the translational movement between the knee's femoral component and tibial component; while allowing axial pivoting about the lateral compartment during the first half of the flexion cycle, then later in the flexion cycle switching to axial pivoting about the medial compartment.

It is an object of the invention is to make the lateral compartment the stable axial pivot point for weight bearing (high stress) dynamics of the knee (first half of the flexion cycle) during walking and running.

It is an object of the invention is to provide a femoral implant design in which both the medial and lateral condyles have various spheres or spherical portions of identical or different spherical radii that contact the reciprocal tibial implant as the knee moves.

It is an object of the invention is to provide a femoral implant design in which the lateral condyle may have a single radius of curvature for the arc as flexion moves from −10 degrees (or more) of hyperextension to 75 degrees of flexion (total=85°).

It is an object of the invention to provide a femoral implant design which may have a patellar-femoral groove with a constant coronal radius of curvature to allow maximal surface contact of a highly congruent hemispherical or domed patellar implant.

It is an object of the invention is to provide a femoral implant design which may have a patellar-femoral groove that extends posteriorly between the femoral condyles to maximize surface contact with the patellar implant to at least 100 degrees or more of flexion.

It is an object of the present invention is to provide a femoral implant design which may have a patella-femoral groove that is slightly lateralized between the medial and lateral condyles as it tracks distally and posteriorly between the femoral condyles, when tracking back proximally on the femur, the patella tracks slightly more laterally (2-10 degree angle) allowing stable patella tracking throughout extension and flexion.

It is an object of the invention to provide a single knee implant design that provides the surgeon with the flexibility to preserve or resect the posterior cruciate ligament (PCL). In the case of resection of the PCL, the knee prosthesis of the present invention offers advantages over a traditional PCL substitution type design (i.e., a design with a traditional cam and post): a) by being more bone preserving as the bone in the intercondylar recess is not removed to accommodate a housing, b) the patellar groove is also able to be further extended along its track (lowering patellar implant stress) since no femoral housing is needed, c) the patellar dislocation safety factor (dsf) is also increased in this invention (to 10 millimeters or more) at all angles of flexion, whereas traditional PCL substitution type design can be less stable.

It is an object of the invention to provide the surgeon more flexibility of implantation since the implant has a wide range of acceptable femoral-tibial axial alignments which allows the tibial component to be positioned freely for more optimal bone coverage without limiting axial rotation of the knee (since the implant moves freely in axial motion), thus making this design easier for the surgeon to implant consistently with excellent bone coverage and the desired functional results.

It is an object of the invention is to provide a femoral implant that may be designed to articulate with a traditional ultra-congruent (anterior-posterior lipped) tibial insert, or a lateral pivoting tibial insert or a mobile bearing (medial & lateral congruent) tibial insert; all of which can assemble into a metal tibial base and also may be either stationary or mobile. This flexibility provides the surgeon with significant versatility to treat a variety of patient indications using the same knee system and instrumentation thereby expanding the treatment option intra-operatively for the surgeon, without compromise.

It is an object of the invention is to provide a knee prosthesis that can also be used in conjunction with a 'cam and post' mechanism in order to yield a more traditional stabilized design when collateral ligaments are deficient or other major instability exists.

It is an object of the invention to provide a femoral implant with a lateral condyle possessing a spherical radius that matches the reciprocal radius of the lateral tibial surface, thus creating a stable 'ball and socket' type articulation for this compartment during weight bearing activity (the first half of the knee flexion cycle).

It is an object of the invention is to provide a tibial implant that may have a medial surface with a curved 'half-pipe like' surface which sweeps in an arcuate fashion allowing the medial femoral condyle to rotate freely while maintaining excellent contact with the this tibial surface. This implant shape allows the smooth axial knee motion with the knee pivoting around the lateral compartment while sweeping a smooth arc in the medial compartment during weight bearing flexion activity of early flexion. This implant provides a minimum of at least 5 degrees internal and 10 degrees external tibial axial rotation with respect to the femur which is an improvement in function over most existing designs.

It is an object of the invention to provide a tibial implant whose anterior aspect may have a gentle anterior bevel to better accommodate the patellar ligament without impingement.

It is an object of the invention to provide a tibial implant that has a PCL recess in the posterior aspect to allow the PCL to be easily retained without removing excess bone from its origin.

It is an object of the invention to provide a tibial implant that may have a beveled posterior-lip located at the posterior aspect of the tibial insert which enables greater knee flexion while maintaining stable anterior/posterior translation while avoiding impingement of femoral bone on the tibial component.

It is an object of the invention to provide maximal tibial surface contact area in both the lateral and medial knee compartments thereby reducing stress and wear.

It is an object of the invention to provide a knee prothesis with means to control anterior-posterior translation of the femur on the tibia with 'ball & socket' capture of at least one condyle at any time during flexion especially during high energy activities making the knee function significantly more stable and efficient.

BRIEF DESCRIPTION OF THE SEVERAL VIEWS OF THE DRAWINGS

flexion.

DETAILED DESCRIPTION OF THE INVENTION

Most existing knee replacement designs attempt to restore normal function to the damaged, arthritic knee at the cost of mechanical failure of the implant as exemplified by poor motion, poor durability (increased wear), and poor strength. Much of this inadequate function and lack of durability is due to the inability of existing designs to really restore the normal motion pattern to the abnormal, aging arthritic knee. These designs by attempting to force a return to 'normal' on these aging knees, actually create high implant and bone stresses leading to the early failures. This new invention is the result of significant discoveries through studying pathologic wear patterns of arthritis as well as imaging technologies which visualizes and precisely quantify motions inside the living knee (using fluoroscopic, CT and/or MRI) for different disease and injury states. Therefore, this invention could be designed with special insight to enhance existing motion patterns into controlled, consistent patterns which properly engage the quadriceps and hamstring muscles while providing a stable articular surface thus avoiding the pitfalls of many present designs.

In the context of the knee, a stable joint is one in which unintended slippage or sliding is limited between the lateral and medial condyles of the femur and their respective lateral and medial tibial compartments. Some sliding of the each condyle within its elongated compartment is required due to the complexity of motion in the knee. However, the sliding in this design is controlled by always having one condyle anchored in 'pivot' mode so that the knee experiences no unnecessary, inefficient motion. In this invention, the knee while in the first half of flexion is stabilized (pivots) laterally with a gradual shift to medial stabilization (pivots) as the knee goes to high flexion activities.

Another source of knowledge driving this new invention are reports of carefully documented measurements of knee wear patterns (foot-prints') in these aging, ligament deficient, and arthritic knees. Observing these 'foot-prints' gave insight for this invention to replace the arthritic surfaces of the knee in an extremely efficient and functional manner while restoring the leg's alignment deformity. Also, by maintaining existing ligaments/muscles and using implant surfaces to guide and limit the existing erratic arthritic motion pattern in an functional matter thus improving function for the active patients in walking, stair climbing, kneeling, squatting, etc., (without requiring a 'cam/post' implant mechanisms as seen in many existing designs which can create increased wear and stress in the implant).

The present invention capitalizes on the natural asymmetrical configuration between medial and lateral compartments of the knee. In initial flexion (first half of the flexion cycle about 0-75 degrees), the lateral knee compartment has a generally congruent, spherical contact for lateral axial pivoting during the activities of walking and stair or hill climbing, then becoming less congruent with later, higher flexion activities such as squatting, lunging or kneeling the axial pivot point shifts medially allowing more posterior migration of the medial femoral condyle on the tibia to accommodate these maximal flexed states).

The present invention has a medial compartment that is more open and allows the femoral medial condyle to sweep out an arc similar to a large ball or sled traveling down a curved trough, 'half-pipe' or luge track 40. This configuration induces the femoral component to freely rotating outward toward the patella (attached at the tibial tubercle which sits anterolateral on the tibia) leading to early engagement of the quadriceps/patellar mechanism and a positive lock of the patella into its groove (and quadriceps muscle) between the femoral condyles. This stable knee motion allows for quadriceps and hamstring muscles to function at their strongest position as the knee flexes and extends. The implant's congruent articular surfaces prevents slippage and allow patients to return to their desired activities quicker and better after knee replacement. This invention accomplishes all of this under low wear and low stress conditions for this novel implant to have long-term durability.

Figure 6:
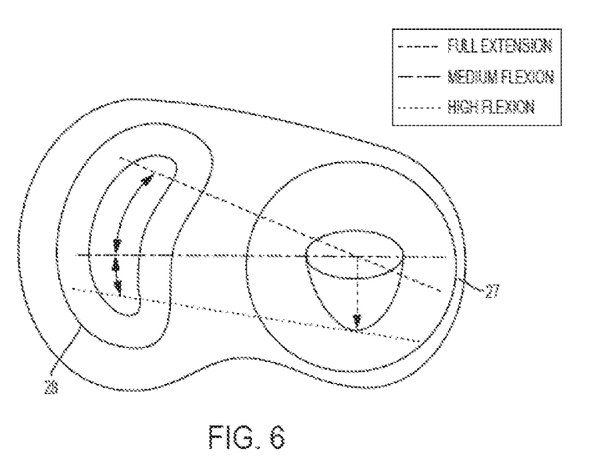
FIG. 6 shows the motion of the medial condyle on the tibial plate during flexion.

Each femoral condyle has two main radii (total of four) with the distal medial condyle having the largest of these condylar radii located distally therefore contacting the tibia at the point of full extension, thus allowing the medial condyle to have maximum congruency with the anterior portion of the 'half pipe' medial tibial compartment. (See FIGS. 6, 9 and 14) The smaller medial condyle radius and the medial tibial compartment transition to more of a 'ball and socket' at flexion above 75 degrees (second half of the flexion cycle). The medial condyle shrinks in radius beginning at a point of flexion about 75 degrees and the congruency is increased such that the medial condyle is able to enter the more congruent 'ball & socket' portion of the medial tibial surface located posteriorly, thereby allowing the pivot point to shift to this medial position and allow the tibia to rotate more externally gaining higher flexion as the medial condyle pivots about this medial point. As noted above, the patella locks into the patella groove with maximizing stability.

According to the present invention, the two main radii of the lateral condyle will be smaller than the corresponding two main radii of the medial condyle. This provides optimal surface area (smaller lateral compartment) for maximum congruency in the lateral compartment for axial pivoting, which minimizes or eliminates sliding on the lateral side during early flexion. The larger of the lateral condyle radii is the distal portion of the lateral condyle which has full contact the tibia at extension. The smaller lateral condylar radius is the posterior portion which contacts the tibia at flexion greater than 75 degrees and allows this condyle to escape the full congruency of the lateral hemispherical surface and slide forward in cooperation with the medial pivoting (creating the ability for the tibia to rotate externally) gaining higher flexion.

The present invention enhances lateral axial pivoting in the arthritic, ligament deficient knee as it flexes during high stress activities of walking and running. This motion is opposite (i.e., laterally rather than medially) of a normal healthy knee in most weight bearing activities (high load) such as walking/running. Later, during the higher flexion activities, the articular design shifts the axial pivot point medially allowing the knee contact points to move posterior with the additional external tibial rotation, thereby avoiding bone impingement and improving range of motion (ROM).

In the present invention, knee strength is also improved by how this invention improves the dynamic alignment and mechanical advantage of the quadriceps mechanism. This is accomplished by the variable axial pivoting motion which keeps the patella/quadriceps muscle facing the femoral-patellar groove throughout the range of motion while the contact points move posteriorly, increasing the muscle moment arm, thus creating a very powerful, stable articulation during walking, stair climbing and sit to stand activities.

The present invention improves durability of the knee by cooperating and controlling the existing arthritic knee motion rather than trying to force it to be like a normal, healthy, intact knee. This design provides increased, congruent knee contact surfaces which are more stable, creating contained motions that reduce the stresses on the articular surface and bone implant interfaces during activities like walking, stair climbing and sit to stand. The design provides complete congruent surface-to-surface contact in the lateral knee compartment (upper surface of a tibial component and the condylar surface of a femoral component) throughout early knee flexion during walking and running. This lateral pivot during early flexion causes the femur to face and engage the patella/quadriceps muscle which powers the knee in these dynamic weight bearing, high stress activities. Then later (after 75 degrees) the pivot point switches more medially allowing more congruency medially while still allowing the posterior shift of the femur on the tibia for higher flexion of the knee.

The present invention provides a knee prosthesis specifically designed with a variable pivots as the knee moves through full ROM for various activities. This is done by initially restricting the translational movement laterally while allowing free axial rotation in this lateral knee compartment, and then later in the flexion cycle shifting to a medial pivot point which enhances posterior translation and high flexion capacity for kneeling, squatting or lunging activities over 75 degrees of flexion.

This present invention provides a femoral implant design that may have a patellar groove that is slightly lateralized between the wider medial condyle and the narrower lateral condyle creating this intercondylar groove for the patella to track. With flexion, the patella begins posterior and distal, then travels anterior and proximal with extension (also slightly lateral at ~2-10 degree angle) in the groove across the femoral implant's anterior surface. In the reverse as flexion occurs, the patella begins in the shallow proximal femoral groove and then travels to the deepened groove distally and posteriorly between the condyles with flexion thus 'harnessing' the powerful patella/quadriceps mechanism as a the major driver of knee motion.

In this invention, the knee moves with an axial pivot point located laterally in the first half of the flexion cycle, before switching to a more medial axial pivot point during the latter half of the flexion cycle enhancing and optimizing (but not normalizing) the motion and contact area for improved function of the aging, arthritic knee.

In one embodiment the femoral implant design has a lateral condyle which may have a single radius of curvature from 10° or more of hyperextension to 75° (85° total) or more of the flexion cycle.

In another embodiment the femoral implant has a lateral condyle which may have one radius of curvature for the first 50% of the range of motion (−10° to 75°) and a second smaller radius of curvature for the second 50% of the range of motion (75° to 150°).

In one embodiment the medial condyle may have one radius of curvature for the first 50% of the range of motion (−10° to 75°) and a second smaller radius of curvature for the second 50% of the range of motion (75° to 150°). In mid-flexion the smaller radius is able to track posterior along the tibial implant surface and to later reach the posterior pivot point as the knee is flexed.

In most instances and in this design, it is preferred for the femoral implant to have a patellar femoral groove with a constant radius of curvature in the coronal plane that allows articulation of a highly congruent hemispherical or domed patellar implant. The patellar groove extends posteriorly to enable optimal surface contact area (with lower stresses) for the patellar implant for at least 100 degrees or more of flexion.

The femoral implant may be designed to articulate with either a traditional anterior/posterior lipped (ultra-congruent) 'PCL sacrificing' tibial insert, or a variable pivot (lateral then medial) congruent (PCL sacrificing or sparing) tibial insert, both of which assemble into and are stationary with a metal tibial base. This also may work with a mobile bearing (medial & lateral congruent) design which may include the stable pivoting features. This flexibility provides the surgeon with significant versatility to treat a variety of patient indications with the same knee system and the same instrumentation while easily varying the treatment option intra-operatively, without compromise or the need for more implant inventory and extra instruments.

The present invention is comprised of a single femoral, patellar and tibial (base plate with insert) implant design that provides the surgeon with the flexibility to preserve or resect the posterior cruciate ligament (PCL). In the case of resection of the PCL, this knee prosthesis offers the following advantages over a traditional PCL substitution type design (i.e., a design with a traditional cam and post): a) the knee prosthesis of the present invention is more bone preserving as the bone in the inter-condylar recess is not removed to accommodate an implant housing, b) the patellar groove is further extended posteriorly and lateralized on the femoral component (improving stability and wear characteristics) since no implant housing is required, c) the dislocation safety factor (dsf) is also improved over existing designs (>10 millimeters or more at all angles of flexion).

The tibial implant has reciprocal hemispherical surfaces located in the posterior one third of the tibial insert (matching the-radii of the femoral condyles). The posteriorly located congruent surface laterally provide the fulcrum during early flexion while the congruent surface medially during high flexion, avoids impingement of femoral bone on the tibial component and at the same time minimize anterior/posterior translation (slippage) allowing for increased leverage and strength. In most embodiments the tibial implant has a lateral proximal surface possessing a hemispherical shape that matches the larger of two spherical radii of the lateral femoral condyle creating a functional 'ball and socket' articulation for weight bearing activities (first half of the knee flexion cycle=−10° to 75°).

The medial tibial surface may have a 'half-pipe' shaped surface in its anterior $\frac{2}{3}^{rd}$ that in the coronal (frontal) plane possesses the same radius as the spherical portion of implant's medial femoral condyle which provides excellent articular contact (low stresses) during the arcuate sweeping motion of this medial condyle as pivoting occurs about the lateral compartment (allowing the femur to axially rotate on the tibia at least 5 degrees internally and 10 degrees externally(total=15 degrees).

The tibial articular surface optionally has a gentle beveling of the anterior lip to accommodate the patellar ligament in flexion preventing impingement and damage. There may also be PCL recesses both in the medial edge of the posterior lateral femoral condyle as well as the tibial tray to allow the PCL extra freedom of motion.

The surface of the tibial implant of the present invention has two hemispherical radius in the lateral compartment; one in the posterior one third and another in the anterior two thirds which captures the matching lateral femoral condyle's two spherical radii in a stable fashion through knee flexion and axial pivoting with optimal muscle leverage while avoiding tibial impingement of femoral bone posteriorly which occurs when femoral component is positioned to far anterior on the tibial component.

The present invention reduces the need for separate implant designs to accommodate different existing arthritic conditions regardless of cruciate ligament damage; i.e does not require a posterior-stabilized (PS version with post/cam design) implant requiring a different surgical tools as well as different implants(more inventory).

The tibial and femoral implants of the present invention may be made out of any suitable biomaterial having the required mechanical and biological properties. Most preferably they are made from one or more of new biomaterials such as ultra-high molecular weight polyethylene (UHMWPE), cross linked polyethylene with vitamin E, metallic materials such as cobalt-chromium or titanium, but may be formed from other materials, such as metals, a ceramic material, a polymer material, a bio-engineered material, carbon fiber, nylon, glass, polyethylene, polyester, polytetrafluoroethylene or the like, in other embodiments. These materials may be used alone or in combination.

The surgery for implantation is less extensive than required for existing knee designs because the patient's remaining ligaments and bone are left largely intact. The present design also avoids lateral release of the patella as a required surgical step because the knee implant of the present invention dynamically aligns the femoral patella groove with the natural lateral position of the tibial tubercle and patella/quadriceps mechanism. The present design can be personalized during implantation to a patient's own anatomy and knee motion. The surgeon is provided more flexibility in terms of axial alignment of the knee implants allowing the surgeon more optimal tibial bone coverage without constraining rotational alignment, (freely pivoting) thus making this design easier for the surgeon to implant yet consistently obtain excellent function and results.

An embodiment of the knee prosthesis 1 of the present invention is shown in FIGS. 1-11 as described below.

Figure 1:
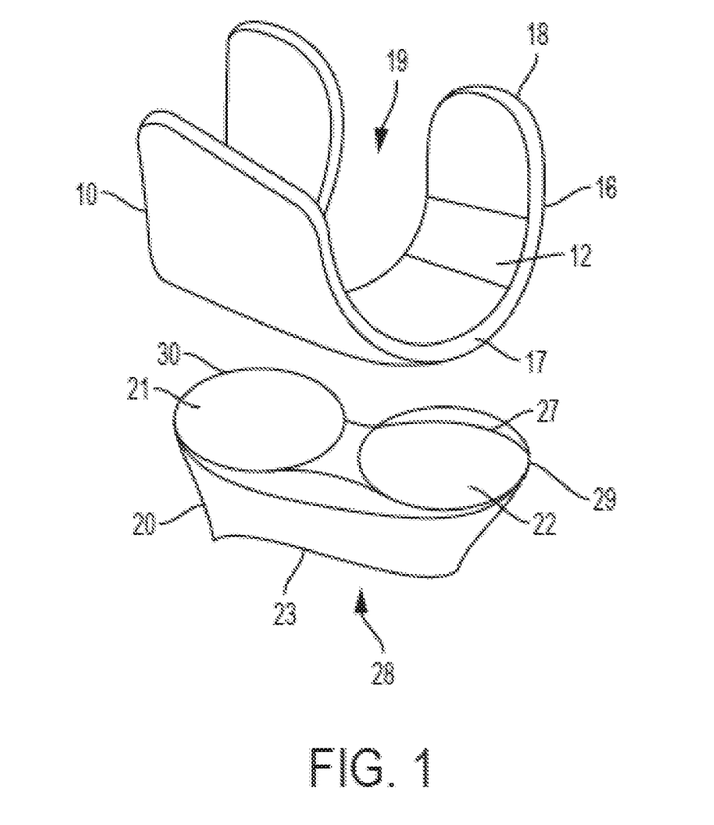
FIG. 1 is a view of a knee prosthesis.

Referring to FIG. 1, a femoral component 10 mounts to the distal end of the femur 12 and a tibial component 20 for mounting to the proximal end of the tibia 21 for articulating with the femoral component.

The femoral component 11 includes a lateral condyle portion 13, a medial condyle portion 14 and a patellar flange portion 15 which joins the anterior ends of the lateral and medial portions 13, 14. The lateral and medial condyle portions 13, 14 being substantially parallel and spaced apart from each other for form a recess 19. Each of the lateral and medial condyle components 13, 14 has an outer surface 16 for articulating with the tibial component 20.

Figure 4:
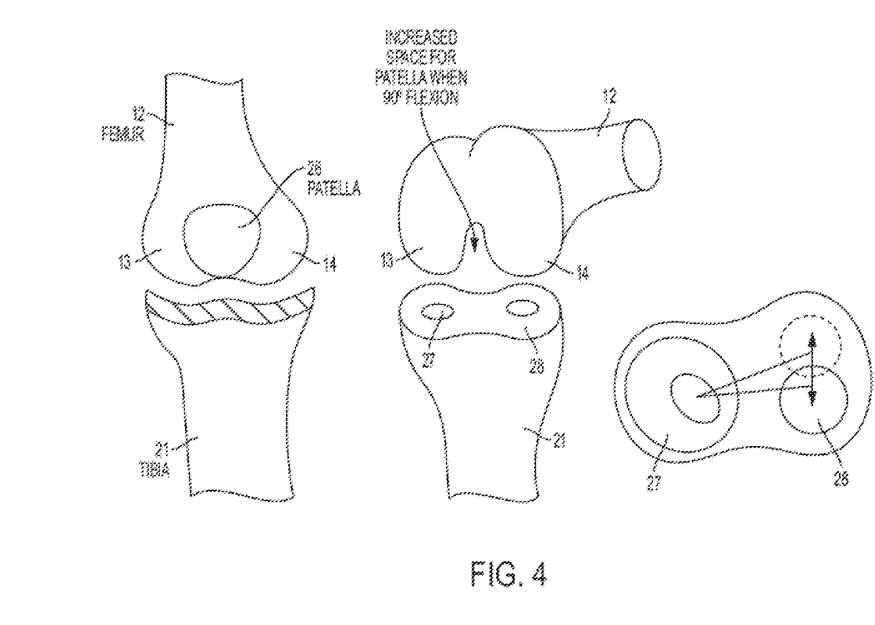
FIG. 4 shows the motion of the medial condyle in its socket during the first 50° of flexion.

The outer surface 16 of each condylar portion 13, 14 preferably has a distal portion 17 for articulatingly engaging a portion of the tibial component 20 when the knee joint is extended and partially flexed as shown in FIG. 4, and a posterior portion 18 for articulatingly engaging a portion of the tibial component 20 when the knee joint is flexed substantially 90 degrees as shown in FIG. 4.

The femoral component 11 may include typical attachment aids for helping to secure the femoral component 11 to the distal end 10 of the femur 12. Such attachment aids may include one or more pegs, fins, surface treatments, etc., as will now be apparent to those skilled in the art.

The femoral component 11 may be constructed in various manners and out of various materials as will now be apparent to those skilled in the art. Thus, for example, the femoral component 11 can be machined, cast, forged or otherwise constructed as a one-piece, integral unit out of a medical grade, physiologically acceptable metal such as a cobalt chromium alloy or the like, in various sizes to fit a range of typical patients, or may be custom-designed for a specific patient based on data provided by a surgeon after physical and radiography examination of the specific patient, etc.

The tibial component 20 includes a base or tray member 23 for being secured to the proximal end 24 of the tibia 25. The tibial component 20 can be constructed so that it is directly attachable to the proximal end of the tibia 24 or it may be designed to mount to a separate base plate, not shown.

Figure 8A:
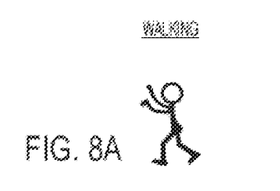
FIGS. 8a-c shows the position of the tibia, femur and patella in partial flexion (walking).

The tibial component 20 preferably includes attachment aids for helping to secure it to the proximal end 21 of the tibia 19. Such attachment aids may include one or more pegs, fins, screws, surface treatments, etc., on the lower surface of the tibial component thereof as should be readily apparent to one skilled in the art. In one such embodiment a peg 26 is used as shown in FIG. 8.

The tibial component 20 may be constructed in various manners and out of various materials as will now be apparent to those skilled in the art. Thus, for example, it can be machined or otherwise constructed as a one-piece, integral unit out of a medical grade, physiologically acceptable metal such as a cobalt chromium alloy or the like, in various sizes to fit a range of typical patients, or may be custom-designed for a specific patient based on data provided by a surgeon after physical and radiography examination of the specific patient, etc. The upper surfaces may have various finishes applied including highly polished for load bearing surfaces.

The tibial component 20 has an upper bearing surface 27, a lower or distal surface 28, a medial side 29, a lateral side 30, an anterior or front side 31, and a posterior or rear side 32. The lower surface 28 is designed for mating to the tibia 25 or to a base plate. The sides 28, 29, 30 and 31 of the tibial component 20 preferably has a generally angle upward and outward from the lower surface 28 to the upper surface 27 thereof.

The upper bearing tibial surface has a generally hemispherical lateral compartment a 21 for pivotally receiving and coacting with the outer surface 16 of the lateral condyle portion 13 of the femoral component 11, and a medial compartment 22 for pivotally receiving and coacting with the face surface 16 of the medial condylar portion 14 of the femoral component 11. The lateral compartment 21 retains the lateral condyle portion 13 in a ball and socket type of arrangement in early flexion. The medial compartment 22 while shaped to receive the medal condyle portion 14, is elongated such that the medial condyle portion 14 can slide in the medial compartment 14 during motion of the knee. The medial and lateral compartments are sufficiently congruent to allow adequate surface contact with the medial and lateral condyle portions for proper support.

The tibial component 20 includes congruency for restricting the slid-able movement of the articular bearing member 45 relative to the base member 43 but allows a swinging motion in the medial portion of the upper surface 67 of the articular bearing member 45 with a pivotal motion of the lateral portion of the upper surface 67 of the articular bearing member during early flexion 45. The restriction means may be designed to restrict the pivoting motion of the articular bearing member 45 to approximately 20 degrees of internal/external rotation of the knee joint 13 as will now be apparent to those skilled in the art. The restriction means may be constructed or formed by various structure.

One of skill in the art will appreciate that the medial and lateral condyle portions 13, 14 can be placed on the tibial component 22 and the bearing surfaces can be placed on the femoral component 11.

The method of replacing a knee joint using the joint prosthesis 1 of the present invention typically starts with standard preoperative planning to estimate the size of the prosthesis to be implanted. The knee joint can then be exposed in any typical manner. The distal end 10 of the femur 12 and the proximal end 24 of the tibia 25 can then be resected and prepared, and a trial reduction of the knee joint performed using appropriate trial implants. Upon successful trial reduction, an appropriate femoral component 11 is implanted on the prepared distal end 10 of the femur 12, and an appropriate tibial component is implanted on the prepared proximal end 24 of the tibia 25. After final testing for motion and stability, the surgical site can be closed in any typical manner.

Using the present invention, the posterior cruciate ligament (PCL) 41 can be readily retained to provide more stability along with the medial collateral ligament 42 (MCL) and lateral collateral ligament (LCL) 43.

Figure 2:
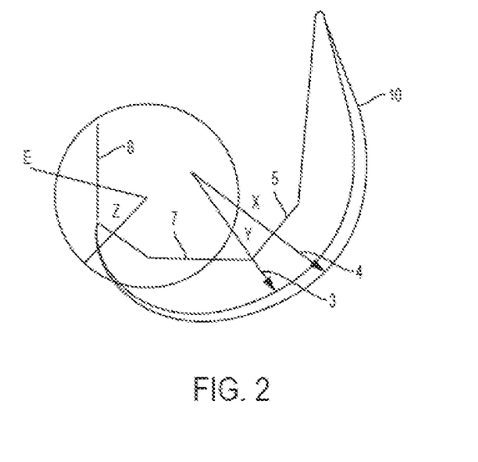
FIG. 2 is a side view of the femoral component of the knee prosthesis showing multiple radii.
Figure 3:
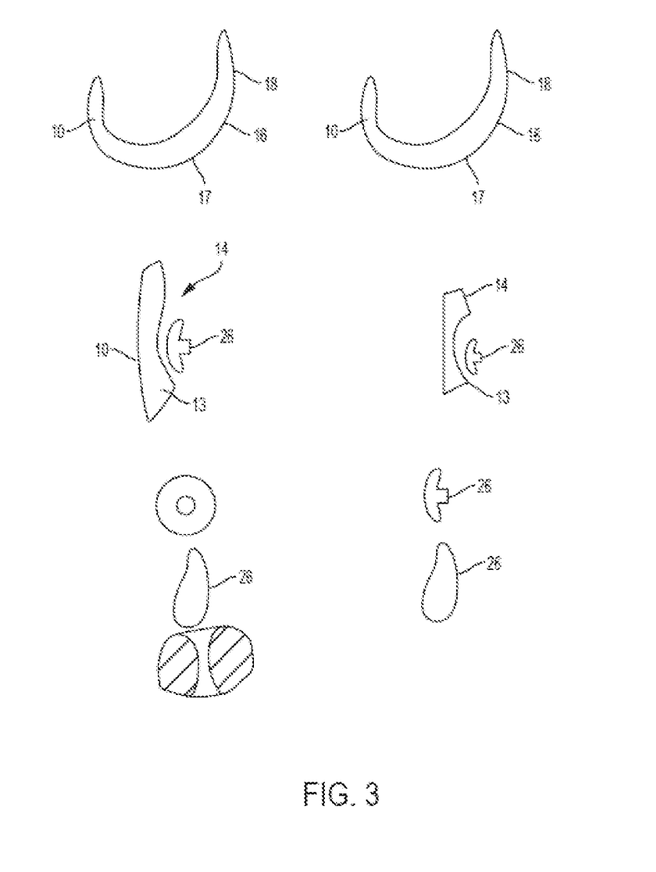
FIG. 3 shows the lateralizing and naturalizing of the femoral patellar groove.

Referring to FIGS. 2 and 3, the width of the lateral condyle 13 is smaller than the width of the medial condyle 14 thereby shifting the patellar groove laterally. This is more natural for the laterally positioned patella thus provides increased stability and lower stress for the femoral-patellar joint.

Referring to FIG. 4, which show the position of the patella 26 in the patella groove 19 during extension and flexion. The sliding motion of the medial condyle 14 during the first 75° of flexion is shown in FIG. 5.

Figure 5:
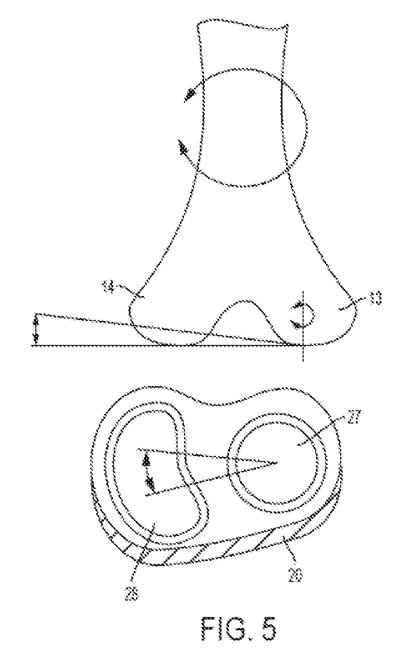
FIG. 5 shows the motion of the medial condyle in the first 50° of flexion.

Referring to FIG. 5 the differences in motion of a knee of the present invention can be observed. In extension the lateral and medial condyle portions 13, 14 of the femoral component 11 are in full contact with the lateral and medial concavities 27, 28.

In early flexion, the femoral component 11 pivots laterally rolling out (externally) to align with the patella 26 and the quadriceps 40 while the medial condyle portion 14, slides anteriorly along the medial tibial 'half-track' surface 28. For the first 75 degrees or so of motion, the lateral femoral condyle 11 and the lateral tibial surface 20 are rotating congruently with full contact. Beginning at about 75 degrees the tibial and femoral components laterally begin to lose congruency with the motion becoming a sliding motion allowing translational motion to occur laterally with the axial pivot point shifting medially.

Figure 7A:
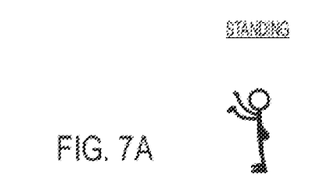
FIGS. 7a-c shows the position of the tibia, femur and patella in full extension (standing) with the present invention.
Figures 7B, 7C:
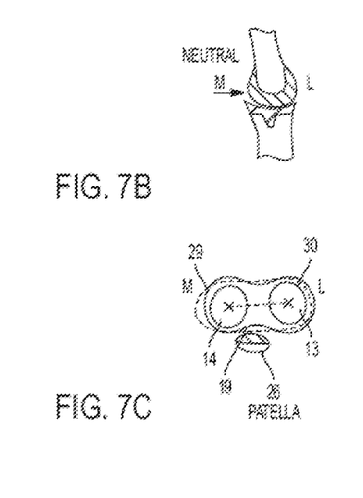

Referring to FIGS. 7a-c that show a relatively equal and centered weight distribution between the medial condyles 14 and the lateral condyles 13 on the medial compartment 29 and the lateral compartment 30 while a person is standing without movement. When standing the patella 26 is centered in the patellar groove 19.

Figure 8B:
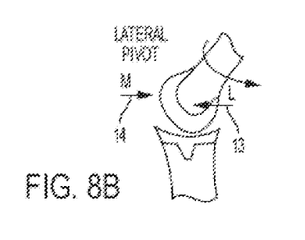
Figure 8C:
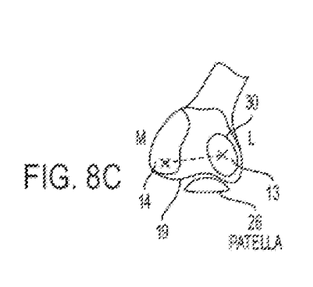

Referring to FIGS. 8a-c which shows a lateral pivot while a person is engaged in walking activity, the patella 26 and its femoral groove align accomplished by this external femoral rotation created as the knee pivots laterally through a range of motion from about −10° to about 75°.

Figure 9A:
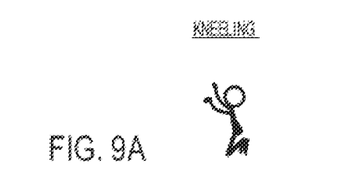
FIGS. 9a-c show the position of the tibia, femur and patella in the present invention when in full extension (kneeling).
Figure 9B:
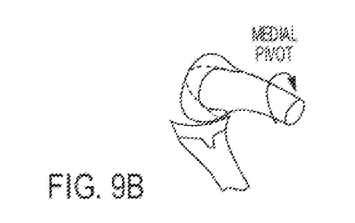
Figure 9C:
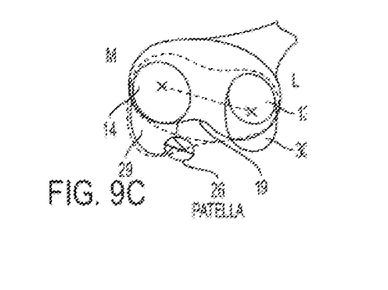

Referring to FIGS. 9a-c which shows the knee in a medial pivot at a range of motion over 75° as might be observed in kneeling or squatting. At this level of flexion, the medial condyle 13 becomes the axial pivot point on the posterior medial tibial hemispherical surface in this medial compartment 29 and the patella travels in the deepened portion of the femoral-patellar groove 19.

In all ranges of motion, the patella remains locked in the patellar groove (stronger locking with more flexion) 19.

A knee prosthesis for replacing at least a portion of a knee joint between the distal end of a femur and the proximal end of a tibia, the knee prosthesis comprising a femoral component for mounting to the distal end of a femur comprising a lateral and a medial condyle, each condyle having a major (first) and minor (second) radius (a total of four condylar radii: two medially & two laterally on the femoral component). The major radii of both condyles on the femoral component are located on the condyles distal surfaces while the two minor radii are located posteriorly on each condyle. A tibial component for mounting to the proximal end of a tibia; said tibial component having four recessed areas in its proximal (articulating) surface corresponding to where the four reciprocal radii of the femoral component contact or articulate with said tibial component at various times in the knee flexion cycle. Two of the tibial component recesses are approximately hemispherical and each located in the posterior one third of the tibial component; wherein these posterior recesses provide the stable pivot points with the femoral condyles during knee flexion beginning with lateral axial pivoting in the first half of the flexion cycle and finishing the last half of the cycle with medial axial pivoting. The other two tibial component recesses are oblong in shape and located in the anterior two thirds of tibial component's proximal surface; wherein the anterior recesses are for the non-pivoting femoral condyle to smoothly translate forward rotating around the pivot point creating external rotation of the femur on the tibia during $1^{st}$ half of knee flexion and internal rotation of the femur during the $2^{nd}$ half of the flexion cycle. The lateral tibial hemisphere recess is maximally congruent to the first (major) radius of the lateral femoral condyle engaging in early flexion providing the stable lateral pivot point (and external femoral rotation) during the first half of knee flexion for higher load activities such as walking and running. The medial tibial recess is maximally congruent to the second (minor) radius of the medial femoral condyle during the second half of the flexion cycle providing the stable medial pivot point (for the internal femoral rotation) required for high flexion activities (kneeling, lunging, squatting, etc.). The tibial component having an oblong recessed sections which run anterior to posterior between the posterior and anterior recesses of both the medial and lateral sides of the tibial component where in the recesses occupy the anterior two thirds both medial and lateral tibial surfaces and are roughly shaped like 'halfpipes'; wherein on the medial side, the oblong, half pipe surface is congruent with the first (major) radius of the medial condyle during early flexion as it translates anteriorly allowing the femur to externally rotate engaging the patella/quadriceps power in early flexion. Laterally, the anterior tibial recess is congruent with the second (minor) radius of the lateral femoral condyle as it translates anteriorly during later knee flexion when the pivot point has shifted medially causing the femur to rotate back internally for high flexion activities.

At less than 75 degrees of flexion, the first (major) radii of the both lateral and medial femoral condyles are in contact with the lateral and medial tibial surfaces such that in the lateral knee compartments there is maximal congruency with the posterior hemispherical recess as the pivot point and medially there is smooth contact and anterior translation creating the external rotation of the femur placing the femoral-patellar groove in alignment with the patella.

At flexion greater than about 75 degrees the second (minor) radius of the lateral femoral condyle now begins to translate forward in the anterior lateral recess while the medial femoral condyle translates posteriorly and assumes maximal congruency with the second (minor) medial condyle radius thereby allowing the medial condyle to assume the pivot point during this second half of the flexion cycle creating the internal femoral rotation required for high flexion activities.

In some instances, during the first half of the knee flexion cycle, the articular contact (pivot) point of the knee is centered about a point located generally over the posterior one third of said lateral proximal surface of said tibial component; wherein this articular contact (pivot) point shifts to the posterior surface of the medial knee compartment during the second half of the knee flexion cycle.

In other instances the invention prosthesis allows the femoral component femur to initially pivot externally on the lateral surface of the tibial component quickly aligning the femoral-patellar groove with the quadriceps muscle complex to allow for the capture of the patella to dynamically stabilizing all three components of the knee.

Figure 10:
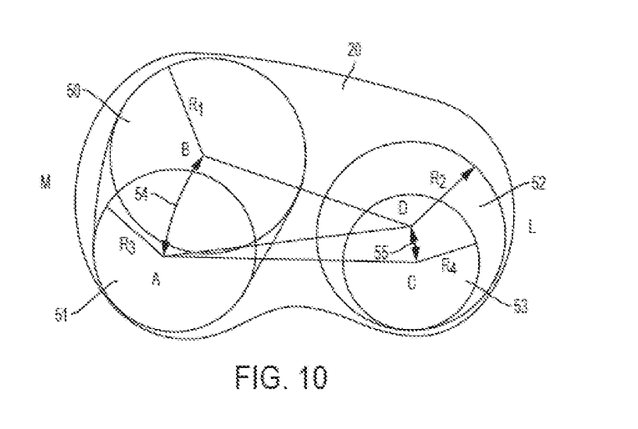
FIG. 10 shows the motion of the femur relative to the tibial plate
Figure 11:
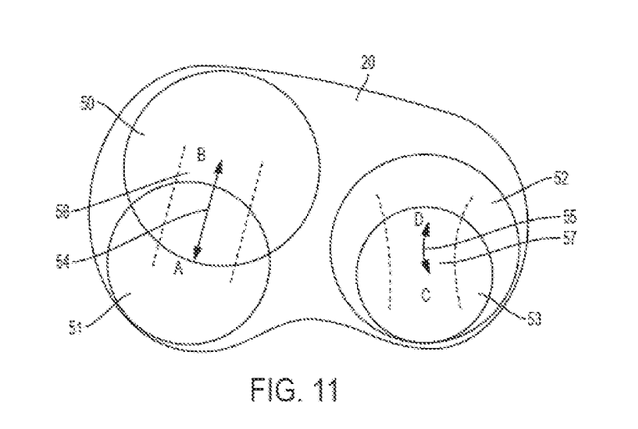
FIG. 11 further shows the motion of the femur relative to the tibial plate with exaggeration of the trough followed by the condyles of the femur.

Referring to FIGS. 10 and 11, in another embodiment the knee prosthesis for replacing at least a portion of a knee joint between the distal end of a femur and the proximal end of a tibia; the knee prosthesis comprises: a tibial component for mounting to the proximal end of the tibia, said tibial component including a proximal surface having a hemispherical lateral surface (posterior one third) and an oblong recess (anterior two thirds) and a medial compartment; and a femoral component for mounting to the distal end of the femur, said femoral component including a lateral and medial condyle each with a major and minor spherical radius for its spherical surfaces. These four spherical radii pivotally coact with the reciprocal medial and lateral recesses in the proximal tibial surface in accordance with claim 1, said hemispherical posterior recess of the lateral surface of said tibial component. and a medial femoral condylar spherical surface whose major radius movably coacts with said medial surface of said tibial component; the minor radius of the said lateral condylar surface located in its posterior portion allows more translation along said lateral tibial surface during the second half of the flexion cycle as pivoting occurs in the medial compartment coacting the minor radius of medial condyle with the corresponding medial tibial surface. There is a distal side, an anterior side, and a posterior side with a spherical shape only from a posterior point on said posterior side of said face surface of said lateral condylar portion to an anterior point on said anterior side of said face surface of said lateral condylar portion located in an arc (radian) of about 85° from said posterior point; said face surface of said lateral condylar portion having a posterior side, a distal side, an anterior side, and a spherical shape; said spherical shape of said face surface of said lateral condylar portion being substantially congruent with said hemispherical lateral surface of said tibial component so that substantially complete congruent surface-to-surface contact between said hemispherical lateral surface of said tibial component and said spherical face surface of said lateral condylar portion of said femoral component is provided throughout the first half of the flexion cycle (of about 85° (−10° to 75°)) of the knee joint; wherein the knee laterally pivots in the first half of the flexion cycle (from about −10° to about 75°) and pivots medially during the second half of the flexion cycle (from about 75° to about 150°). A knee prosthesis in which the variable pivot point of the knee is initially in the lateral knee compartment between the lateral spherical condylar portion (major radius) of the femoral component and lateral hemispherical portion of the tibial component before switching to pivoting in the medial compartment between the spherical (minor radius) of the medial femoral condyle with the posterior hemispherical surface of the medial tibial component during later knee flexion.

In some embodiments the medial condyle portion (major radius) of the femoral component articulates smoothly on the medial sweeping (half-pipe shaped) surface of the tibial component during the first half of the knee flexion cycle.

In another embodiment, the knee prosthesis for replacing at least a portion of a knee joint between the distal end of a femur and the proximal end of a tibia; the knee prosthesis comprising: a tibial component for mounting to the proximal end of the tibia, said tibial component including a proximal surface having a hemispherical lateral surface and a medial surface; and a femoral component for mounting to the distal end of the femur, said femoral component including a first radius portion of a spherical lateral condylar whose face surface pivotally coacts with said hemispherical lateral surface of said tibial component during the first half of the flexion cycle. This lateral condylar portion having a spherical face surface for movably coacting with said hemispherical lateral tibial surface; and being substantially congruent with said hemispherical lateral surface of said tibial component so that substantially complete congruent surface-to-surface contact in this lateral knee compartment between said hemispherical lateral surface of said tibial component and said major radius spherical face surface of said lateral condyle of the said femoral component whose articulation occurs throughout the first half of the knee flexion cycle (from about −10° to 75°) before shifting the pivot point more medial during later knee flexion.

In another embodiment the knee prosthesis for replacing at least a portion of a knee joint between the distal end of a femur and the proximal end of a tibia; the knee prosthesis comprises:
1. a tibial component for mounting to the proximal end of the tibia, said tibial component including a proximal aspect having a hemispherical lateral surface posteriorly for articulating (pivoting) in the lateral knee compartment during the first half of the flexion cycle; and
2. a femoral component for mounting to the distal end of the femur, said femoral component including two sphere-like condyles (medial and lateral) each with two (one major and one minor) radii on their spherical face surfaces; wherein the medial and lateral condylar portions of the invention are designed to pivotally articulate with the tibial component in a variable fashion; first (during the first half of the knee flexion cycle) on the posterior-lateral portion of this tibial component; then later (the second half of the knee flexion cycle) on the posterior-medial portion of this tibial component; wherein as the pivoting articulation occurs in one compartment at a time, therefore in early flexion, there is anterior translation of the medial condyle while in the lateral compartment there is smooth axial pivoting rotation as the knee flexes allowing the necessary engagement of muscles and ligaments in a coordinated, efficient and powerful fashion. These reciprocal hemispherical surfaces of said tibial component with said femoral component allow for congruent articular contact with low stress and low wear between components. Hence the lateral condylar portion has a spherical face surface for movably coacting with said lateral hemispherical surface compartment of said tibial component; this spherical face surface of said lateral femoral condylar having a major radius with spherical shape from about −10° distal to about 75° posterior then transitioning to a minor radius from 75° to about 150°; said major radius portion of the spherical face surface of said lateral femoral condylar being substantially congruent with said hemispherical lateral surface of said tibial component so that substantially complete congruent surface-to-surface contact occurs in said lateral compartment of the knee during the first half of the flexion cycle, thereafter shifting to less congruency in said lateral compartment when the minor radius of the lateral femoral condyle engages the tibial surface, thus allowing smooth anterior translation of this lateral femoral condyle on the tibial component as the axial pivot point shifts medially during the second half of the knee flexion cycle.

Devices of the present invention can be customized using measurements and other data from imaging devices such as a CT scan or MIll. The dimensions of a patient's knee obtained by imaging the knee can be used to size or custom fit the devices of the present invention. The dimensions of the condyles and compartments can be adjusted to better conform to a patient's current geometry or adjusted to correct deficiencies in the patient's current knee geometry. Sizing or customizing a knee using imaging techniques are known in the art and taught in U.S. Pat. No. 8,974,539.

One of skill in the art will appreciate that the dimensions and radii disclosed herein can be varied as long as the resulting joint can transition from a lateral pivot to a medial pivot above about 75° of flexion and the patella is retained in the patellar groove.

I claim:

1. A knee prosthesis comprising:
   (a) a femoral component for mounting to a distal end of a femur comprises a lateral condyle and a medial condyle, each condyle having a major radius and a minor radius for a total of four condylar radii on the femoral component; wherein
      1. the major radii of both condyles on the femoral component are located on a distal surface of the condyles with the major radius of the lateral condyle being equal to or up to 30 percent smaller than the major radius in the medial condyle; and
      2. the minor radii are located posteriorly on the femoral component with the minor radius of the lateral condyle being equal to or up to 30 percent smaller than the minor radius on the medial condyle;
   (b) a tibial plate having medial and lateral sides further comprising:
      1. two hemispherical tibial plate recesses corresponding to the minor medial and major lateral radii lying medially and laterally, each recess is located in a posterior one third of the tibial plate; wherein the posterior recesses provide lateral and medial stable pivot points with the femoral condyles during knee flexion beginning with lateral axial pivoting in a first half of a knee flexion cycle and finishing a second half of the knee flexion cycle with medial axial pivoting,
      2. two oblong tibial plate recesses forming a trough and located in a medial and anterior two thirds of the tibial plate's proximal surface; wherein the anterior recesses are for the femoral condyle to smoothly translate forward rotating around the lateral and medial stable pivot points creating external rotation of the femur on the tibia during the first half of the knee flexion cycle and internal rotation of the femur during the second half of the knee flexion cycle;
      3. wherein the lateral tibial hemispherical recess is maximally congruent to the major radius of the lateral femoral condyle engaging in early flexion providing the stable lateral pivot point for external femoral rotation during the first half of knee flexion for higher load activities;
      4. wherein a portion of the hemispherical medial tibial recess is maximally congruent to the minor radius of the medial femoral condyle during the second half of the flexion cycle providing the stable medial pivot point for the internal femoral rotation required for high flexion activities; wherein on the medial side, a trough surface is congruent with the major radius of the medial condyle during early flexion as it translates anteriorly allowing the femur to eternally rotate, engaging patella/quadriceps power in early flexion; and
      5. laterally, the anterior oblong tibial recess is congruent with the minor radius of the lateral femoral condyle as it translates anteriorly during the second half of knee flexion when the stable pivot point has shifted from lateral to medial causing the femur to rotate back internally for the high flexion activities;
   (c) wherein at less than 75 degrees of flexion, the major radii of both of the lateral and medial femoral condyles are in contact with the lateral and medial tibial troughs such that in a lateral knee compartment there is maximal congruency between the lateral posterior hemispherical recess and the major radius of the lateral femoral condyle providing the stable lateral pivot point and medially there is smooth contact and anterior translation between the femoral condyle and the trough creating the external rotation of the femur placing a femoral-patellar groove on the femur in contact with a patella of the knee;
   (d) wherein at flexion greater than 75 degrees the minor radius of the lateral femoral condyle now begins to translate forward in the anterior oblong lateral recess while the medial femoral condyle translates posteriorly and assumes maximal congruency with the minor medial condyle radius thereby allowing the medial condyle to assume the medial stable pivot point during this second half of the flexion cycle creating the internal femoral rotation required for the high flexion activities;
   (e) wherein during the first half of the flexion cycle the lateral and medial condyles rotate against the tibial plate; and
   (f) wherein during the second half of the flexion cycle the lateral condyle slides anteriorly in the tibial plate.

2. The knee prosthesis according to claim 1, wherein during the first half of the knee flexion cycle, a lateral pivot point of the knee is centered in the lateral knee compartment about a point located over the posterior one third of the tibial plate; wherein the lateral pivot point shifts to the posterior of the tibial plate during the second half of the knee flexion cycle.

3. The knee prosthesis according to claim 1, wherein the prosthesis allows the femoral component to initially pivot externally on a lateral surface of the tibial plate aligning the femoral-patellar groove with a quadriceps muscle complex allowing for the patella to be captured to dynamically stabilize the knee.

4. The knee prosthesis of claim 1, wherein the high flexion activities are kneeling, lunging and squatting.

5. The knee prosthesis of claim 1, wherein the lateral condyle maintains congruent surface-to-surface contact with the lateral hemispherical recess of the tibial plate throughout the first 85° degrees of motion of the knee.

6. The knee prosthesis according to claim 5, in which the major radius of the medial condyle of the femoral component articulates smoothly on the medial trough of the tibial plate during the first half of the knee flexion cycle.

7. The knee prosthesis of claim 5, wherein the 85° degrees of motion of the knee is from −10 to +75 degrees.

8. The knee prosthesis of claim 1, in which a pivot point of the knee is initially in a lateral groove between a major radius of the lateral condyle of the femoral component and the lateral hemispherical recess of the tibial plate before switching to pivoting between the minor radius of the medial femoral condyle with a posterior surface of the medial side of the tibial plate during later knee flexion.

9. The knee prosthesis according to claim 1, wherein said higher load activities are walking and running.

10. A method of stabilizing a knee comprising: mounting a prosthesis for replacing at least a portion of a knee joint between the distal end of a femur and the proximal end of a tibia wherein the prosthesis comprises:
   (a) a femoral component for mounting to a distal end of a femur comprises a lateral condyle and a medial condyle, each condyle having a major radius and a minor radius for a total of four condylar radii on the femoral component; wherein
1. the major radii of both condyles on the femoral component are located on a distal surface of the condyles with the major radius of the lateral condyle being equal to or up to 30 percent smaller than the major radius in the medial condyle; and
2. the minor radii are located posteriorly on the femoral component with the minor radius of the lateral condyle being equal to or up to 30 percent smaller than the minor radius on the medical condyle;

(b) a tibial plate having medial and lateral sides comprising:
1. two tibial hemispherical recesses corresponding to the minor medial and major lateral radii lying medially and laterally, each recess is located in a posterior one third of the tibial plate; wherein these posterior recesses provide lateral and medial stable pivot points with the femoral condyles during knee flexion beginning with lateral axial pivoting in a first half of the flexion cycle and finishing a second half of the knee flexion cycle with medial axial pivoting;
2. Two oblong tibial plate recesses forming a trough and located in a medial and anterior two thirds of the tibial plate's proximal surface; wherein the anterior recesses are for the femoral condyle to smoothly translate forward rotating around the lateral and medial stable pivot points creating external rotation of the femur on the tibia during the first half of the knee flexion cycle and internal rotation of the femur during the second half of the knee flexion cycle;
3. wherein the lateral tibial hemispherical recess is maximally congruent to the major radius of the lateral femoral condyle engaging in early flexion providing the stable lateral pivot point for external femoral rotation during the first half of knee flexion for higher load activities;
4. wherein a portion of the hemispherical medial tibial recess is maximally congruent to the minor radius of the medial femoral condyle during the second half of the flexion cycle providing the stable medial pivot point for the internal femoral rotation required for high flexion activities; wherein on the medial side, a trough surface is congruent with the major radius of the medial condyle during early flexion as it translates anteriorly allowing the femur to externally rotate, engaging patella/quadriceps power in early flexion; and
5. laterally, the anterior oblong tibial recess is congruent with the minor radius of the lateral femoral condyle as it translates anteriorly during the second half of knee flexion when the stable pivot point has shifted from lateral to medial causing the femur to rotate back internally for the high flexion activities;

(c) wherein at less than 75 degrees of flexion, the major radii of both of the lateral and medial femoral condyles are in contact with the lateral and medial tibial troughs such that in a lateral knee compartment there is maximal congruency between the lateral posterior hemispherical recess and the major radius of the lateral femoral condyle providing the stable lateral pivot point and medially there is smooth contact and anterior translation between femoral condyle and the trough creating the external rotation of the femur placing a femoral-patellar groove on the femur in contact with a patella of the knee;

(d) wherein at flexion greater than 75 degrees the minor radius of the lateral femoral condyle now begins to translate forward in the anterior oblong lateral recess while the medial femoral condyle translates posteriorly and assumes maximal congruency with the minor medial condyle radius thereby allowing the medial condyle to assume the medial stable pivot point during this second half of the flexion cycle creating the internal femoral rotation required for the high flexion activities;

(e) wherein during the first half of the flexion cycle, the lateral and medial condyles rotate against the tibial plate; and (f) wherein during the second half of the flexion cycle, the lateral condyle slides anteriorly in the tibial plate.

11. The method of claim 10, in which the major radius of the medial condyle of the femoral component articulates smoothly on the medial trough of the tibial plate during the first half of the knee flexion cycle.

12. A method of stabilizing the knee comprising: mounting the prosthesis for replacing the portion of the knee joint between the distal end of a femur and the proximal end of a tibia according to claim 10 wherein the lateral condyle maintains congruent surface-to-surface contact with the lateral hemispherical recess of the tibial plate throughout a first 85° degrees of motion of the knee.

13. The method of claim 12, wherein in the first 85° degrees of motion of the knee is from −10 to +75 degrees.

14. The method of claim 10, wherein the femoral component and the tibial plate have a variable pivot on a lateral posterior portion of a lateral compartment of the tibial plate during the first half of the knee flexion cycle and on a posterior medial portion of a medial compartment of the tibial plate during the second half of the knee flexion cycle; wherein as a pivoting articulation occurs, anterior translation of the other condyle in the lateral compartment creates a smooth axial pivoting rotation as the knee flexes thereby allowing engagement of muscles and ligaments in a coordinated fashion.

15. The method of claim 14, wherein the lateral condyle has a spherical face surface for movably coacting with the lateral recess of the tibial plate, the spherical face of the lateral condyle having a major radius from about −10° distal to about 75° posterior when the knee is transitioning to the minor radius from 75° to about 150°, the major radius of the lateral femoral condyle being congruent with the lateral recess of the tibial plate so that complete congruent surface-to-surface contact occurs in the lateral compartment of the knee during the first half of the flexion cycle, thereafter shifting to less congruency in the lateral compartment when the minor radius of the lateral femoral condyle engages a tibial surface, thereby allowing smooth anterior translation of this lateral femoral condyle on the tibial plate as the axial pivot point shifts medially during the second half of the knee flexion cycle.

16. A knee prosthesis for replacing a portion of a knee joint between a distal end of a femur and a proximal end of a tibia, the knee prosthesis comprising:

(a) a femoral component for mounting to the distal end of the femur comprises a lateral condyle and a medial condyle, each condyle having a major radius and a minor radius for a total of four condylar radii on the femoral component;
1. the major radii of both condyles on the femoral component are located on a distal surface of the condyles with the major radius of the lateral condyle being equal to or up to 30 percent smaller than the major radius in the medial condyle; and
2. the minor radii are located posteriorly on the femoral component with the minor lateral condyle radius being equal to or up to 30 percent smaller than a minor radius on the medial condyle;

(b) a tibial plate for mounting to the proximal end of the tibia having medial and lateral sides, two troughs which run anterior to posterior which correspond to the lateral and medial condyles of the femoral component; wherein the tibial plate comprises:
1. two tibial hemispherical plate recesses corresponding to the minor medial and major lateral radii lying medially and laterally, wherein each recess is located in a posterior one third of the tibial plate; wherein the two tibial hemispherical plate recesses provide lateral and medial stable pivot points with the femoral condyles during knee flexion beginning with lateral axial pivoting in a first half of the knee flexion cycle and finishing a second half of the knee flexion cycle with medial axial pivoting;
2. Two oblong tibial plate recesses located in a medial and anterior two thirds of a proximal surface of the tibial plate; wherein the two oblong tibial plate recesses are for the femoral condyle to smoothly translate forward rotating around the lateral and medial stable pivot points creating external rotation of the femur on the tibia during the first half of the knee flexion cycle and internal rotation of the femur during the second half of the knee flexion cycle;
3. wherein the lateral tibial hemispherical recess is maximally congruent to the major radius of the lateral femoral condyle engaging in early knee flexion providing the stable lateral pivot point for external femoral rotation during the first half of knee flexion for higher load activities;
4. Wherein the medial trough is maximally congruent to the minor radius of the medial femoral condyle during the second half of the knee flexion cycle providing the stable medial pivot point for the internal femoral rotation required for high knee flexion activities; wherein on the medial side, the medial trough is congruent with the major radius of the medial condyle during early knee flexion as it translates anteriorly allowing the femur to externally rotate, engaging patella/quadriceps power in early knee flexion; and
5. laterally, the anterior tibial trough is congruent with the minor radius of the lateral femoral condyle as it translates anteriorly during the second half of knee flexion when the stable pivot point has shifted from lateral to medial causing the femur to rotate back internally for the high knee flexion activities;

(c) wherein at less than 75 degrees of knee flexion, the major radii of both of the lateral and medial femoral condyles are in contact with the lateral and medial tibial troughs such that in a lateral knee compartment there is maximal congruency between the lateral posterior hemispherical recess and the major radius of the lateral femoral condyle providing the stable lateral pivot point and medially there is smooth contact and anterior translation between the femoral condyle and the trough creating the external rotation of the femur placing a femoral-patellar groove on the femur in contact with a patella of the knee; and (d) wherein at knee flexion greater than 75 degrees the minor radius of the lateral femoral condyle now begins to translate forward in the anterior lateral recess while the medial femoral condyle translates posteriorly and assumes maximal congruency with the minor medial condyle radius thereby allowing the medial condyle to assume the medial stable pivot point during this second half of the knee flexion cycle creating the internal femoral rotation required for the high knee flexion activities.

17. The knee prosthesis according to claim 16, wherein said higher load activities are walking and running.

18. A method of stabilizing the knee comprising: mounting the prosthesis for replacing at least the portion of the knee joint according to claim 16 between the distal end of the femur and the proximal end of the tibia.

* * * * *